United States Patent [19]

Shoesmith, deceased

[11] Patent Number: Plant 6,233

[45] Date of Patent: Jul. 26, 1988

[54] CHRYSANTHEMUM PLANT NAMED DYNAMO

[75] Inventor: Leonard H. Shoesmith, deceased, late of Westfield, England, by May Victoria Shoesmith, executrix

[73] Assignee: Ball PanAm Plant Company, Parrish, Fla.

[21] Appl. No.: 894,305

[22] Filed: Jul. 31, 1986

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Dynamo having white ray florets, deep capitulum, nine week response, strong stems and long peduncles, excellent production, good keeping and shipping quality, and suitability for cultivation in year around programs.

1 Drawing Sheet

The present invention comprises a new and distinct cultivar of *Chrysanthemum morifolium,* Ramat., hereinafter referred to by the cultivar name Dynamo.

Dynamo is a product of a planned breeding program which had the objective of creating new Chrysanthemum cultivars with better characteristics than the well-known cultivar Polaris. Such traits in combination were not present in previously available commercial cultivars.

Dynamo was originated from a hybridization made in a controlled breeding program in Westfield-Woking, England in 1978. The male and female parents are unknown at this time.

Dynamo was discovered and selected as one flowering plant within the progeny of the cross by Leonard H. Shoesmith in November of 1979 in a controlled environment in West Chicago, Ill.

The first act of asexual reproduction of Dynamo was accomplished when vegetative cuttings were taken from the initial selection in February of 1980 in a controlled environment in West Chicago, Ill. by a technician working under formulations established and supervised by Leonard H. Shoesmith. Horticultural examination of selected units initiated in June of 1980 has demonstrated that the combination of characteristics as herein disclosed for Dynamo are firmly fixed and are retained through successive generations of asexual reproduction.

Dynamo has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Dynamo, which in combination distinguish this Chrysanthemum as a new and distinct cultivar:

1. Nine week response.
2. Strong stems with long peduncles up to 30 cm long.
3. Excellent production per stem; up to 14 good usable flowers per stem.
4. Clear white florets; immature florets a pale yellow-green, about 300 florets per capitulum.
5. Florets slightly incurved, with individual florets being up to 35 mm long. The florets are oblong to elliptical with entire margin and obtuse tips. The capitulum is noticeably deeper than Polaris.
6. Capitulum up to 70 mm across.
7. The ability to ship and keep well.
8. Excellent for cultivation in year around programs.

Of the many commercial cultivars known to the present inventor, the most similar in comparison to Dynamo is Polaris. In comparison to Polaris, Dynamo has a thicker or deeper capitulum, thereby presenting a much fuller appearance. Dynamo performs better under low light conditions, and has larger leaves. The color of the florets, response time, and habit of Dynamo are similar to those same characteristics of Polaris.

The accompanying photographic drawing shows typical inflorescence and foliage characteristics of Dynamo, with colors being as nearly true as possible with illustrations of this type. The drawing sheet comprises a black and white photograph which accurately depicts the white floret color. The center florets are colored to accurately show the pale yellow floret color in that region.

In the following description, color references are made to The Royal Horticultural Colour Chart. The color values were determined at approximately 9:00 a.m. on July 2, 1986 under 4000 foot candles of light intensity at Parrish, Fla.

Classification:

*Botanical.*—*Chrysanthemum morifolium,* Ramat., cv Dynamo.

*Commercial.*—Cut cushion spray or cushion pompon.

INFLORESCENCE

A. Capitulum:

*Form.*—Flat.

*Type.*—Decorative.

*Diameter across face.*—70 mm.

B. Corolla of ray florets:

*Color (general tonality from a distance of three meters).*—White.

*Color (both upper and under surfaces).*—155B, center florets 5D.

C. Corolla of disc florets: None present.

D. Reproductive organs:

*Androecium.*—None.

*Gynoecium.*—Present in all florets.

PLANT

A. General appearance:

*Height.*—1-2 meters at finish.

B. Foliage:

*Color (upper surface).*—147A.

*Color (under surface).*—147B.

*Shape.*—Deeply lobed and slightly serrated.

It is claimed:

1. A new and distinct cultivar of Chrysanthemum named Dynamo, as described and illustrated, and particularly characterized by its white ray florets, deep capitulum, nine week response, strong stems and long peduncles, excellent production, good keeping and shipping quality, and by its suitability for cultivation in year around programs.

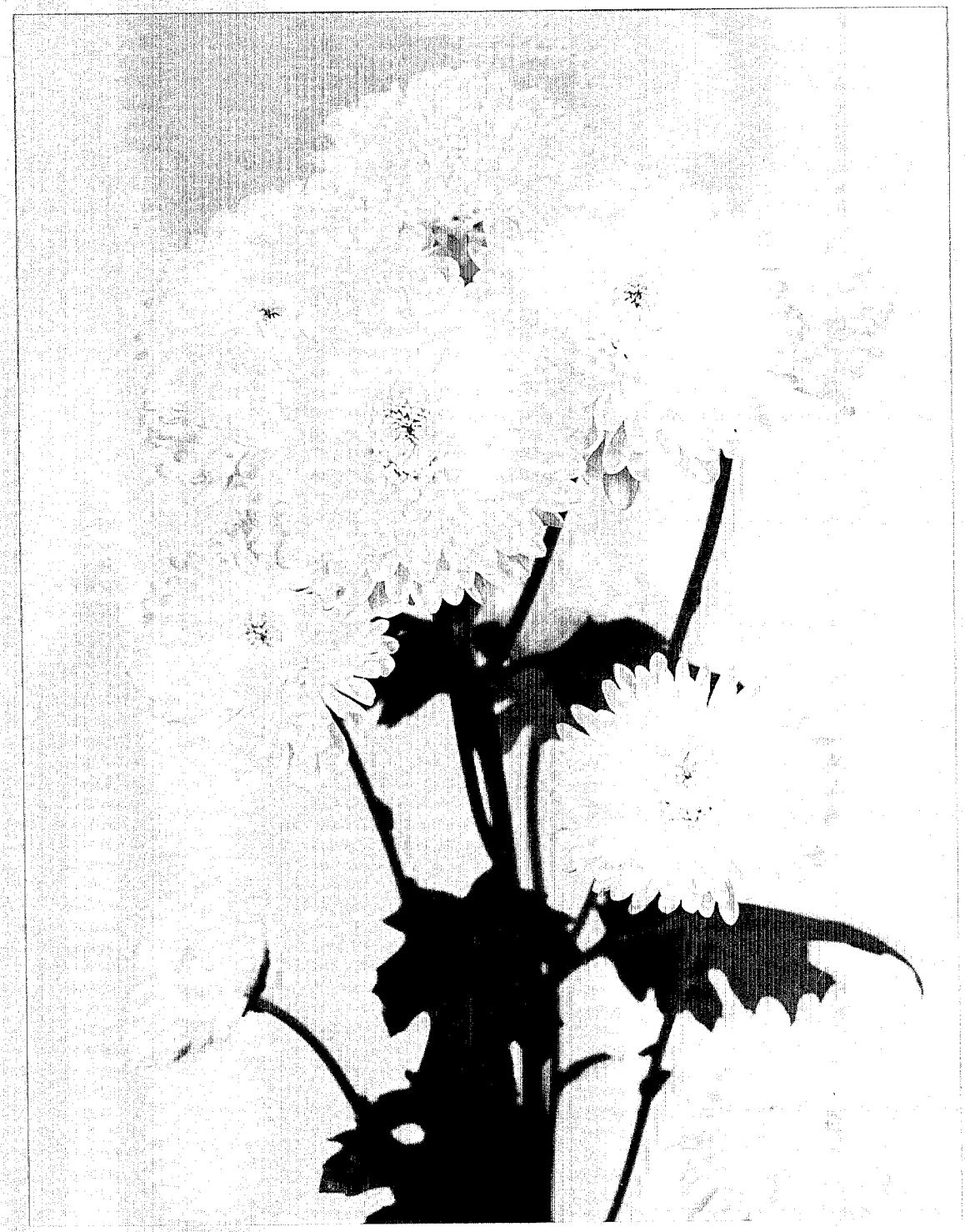

* * * * *